Figure 1:
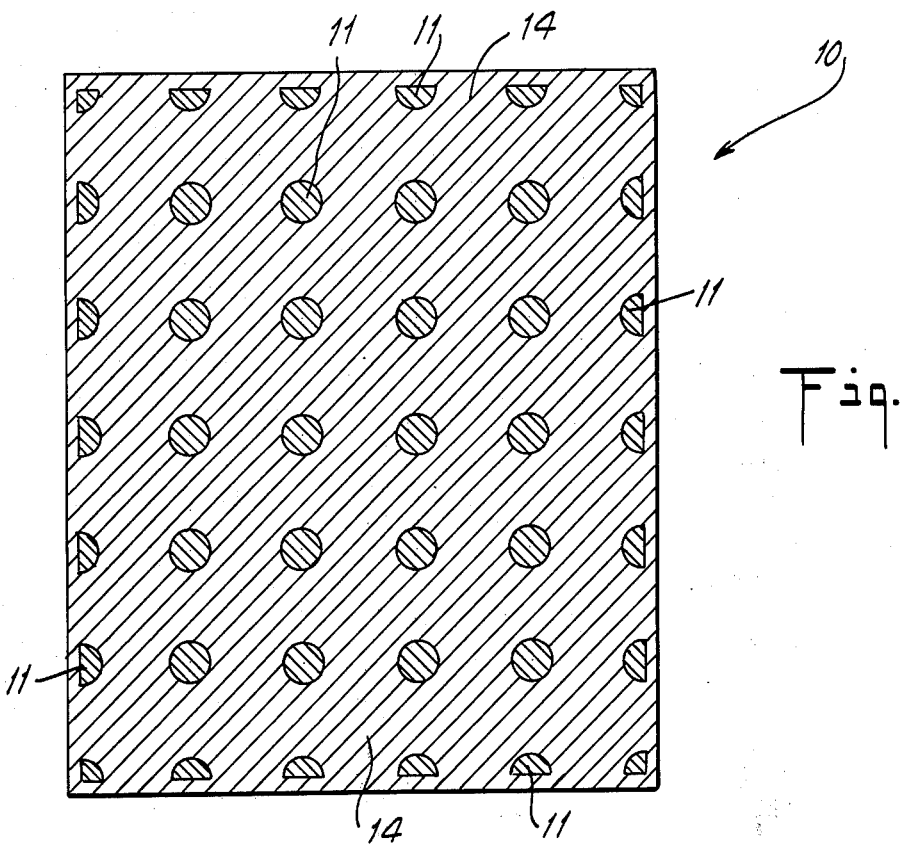

United States Patent [19]

White et al.

[11] 4,075,092
[45] Feb. 21, 1978

[54] HIGH SURFACE AREA PERMEABLE MATERIAL

[75] Inventors: Eugene W. White; William M. Hanusiak, both of State College, Pa.; Rodney A. White, Torrance, Calif.

[73] Assignee: Research Corporation, New York, N.Y.

[21] Appl. No.: 713,258

[22] Filed: Aug. 10, 1976

[51] Int. Cl.$^2$ .................................................. B01D 3/00
[52] U.S. Cl. ............................... 210/22 R; 210/321 B; 260/2.5 R; 195/1.8; 23/258.5 M
[58] Field of Search ................ 210/22, 321 B, 500 M; 264/321, 44, 317 X, DIG. 48; 423/308; 128/92 C; 260/2.5 R; 23/258.5

[56] References Cited

U.S. PATENT DOCUMENTS

| 2,972,349 | 2/1961 | De Wall | 210/22 R |
|---|---|---|---|
| 3,137,611 | 6/1964 | Krolik, Jr. | 264/321 |
| 3,306,967 | 2/1967 | Turkewitsch | 264/321 |
| 3,329,759 | 7/1967 | Rice | 264/321 |
| 3,502,596 | 3/1970 | Sowards | 264/44 |
| 3,505,030 | 4/1970 | Sowards | 264/44 |
| 3,574,646 | 4/1971 | Wismer et al. | 264/44 |
| 3,584,108 | 6/1971 | Nelson et al. | 264/321 |
| 3,775,526 | 11/1973 | Gilmore | 264/321 X |
| 3,833,386 | 9/1974 | Wood et al. | 264/DIG. 48 |
| 3,890,107 | 6/1975 | White et al. | 128/92 C |
| 3,923,940 | 12/1975 | Hujii et al. | 264/317 X |
| 3,929,971 | 12/1975 | Roy | 423/308 |
| 3,998,734 | 12/1976 | Barringer | 55/17 X |

OTHER PUBLICATIONS

Science, vol. 166, No. 3903, Nov. 1969, pp. 1147–1150.

Primary Examiner—Frank A. Spear, Jr.
Assistant Examiner—E. Rollins Cross
Attorney, Agent, or Firm—Cooper, Dunham, Clark, Griffin & Moran

[57] ABSTRACT

Three-dimensional structures providing a plurality of separate interpenetrating, three-dimensional domains or channels or flowpaths, each of said domains or channels or flowpaths being a closed system of connected porosity or permeability and each of said domains or channels or flowpaths being interpenetrating within said structure, have been prepared. These structures are prepared from porous permeable precursor materials having a single three-dimensional domain or channel or flowpath as described above. Suitable precursor materials are provided by the abundant porous carbonate skeletal material of marine life, e.g. the coral Porites skeletal aragonite. For example, by coating the surfaces of such materials with a liquid material capable of being cured or set to a solid, followed by curing or setting and dissolution, e.g. chemical etching, of the coated skeletal material, there is produced a three-dimensional structure in accordance with this invention possessing two separate interpenetrating, three-dimensional domains or channels or flowpaths defined by the residual cured or set coating material. The resulting structure of this invention can be adapted such that a fluid can be applied to one side or face of the structure to flow into and out of such structure via only one of said channels or flowpaths and when so adapted can be employed in apparatus for the treatment or handling of one or more of the fluid streams flowing there-through.

30 Claims, 11 Drawing Figures

HIGH SURFACE AREA PERMEABLE MATERIAL

This invention relates to three-dimensional porous, permeable structures. Porous, permeable three-dimensional structures are known, are found in nature and have been manufactured and employed in industry. For example, three-dimensional structures providing a single three-dimensional domain or channel or flowpath, said domain or channel or flowpath being a closed system of connected porosity or permeability and interpenetrating said structure, are known and have been prepared or replicated from natural materials, see U.S. Pat. Nos. 3,890,107 and 3,929,971, as well as *Science*, Vol. 166: 1147 (1969), *Nature*, Vol. 233: 337 (1971) and *Science*, Vol. 176: 922 (1972). Of some interest in connection with the structure and preparation or replication of porous materials, including control of pore size, see also *J. Biomed. Mater. Res.*, Vol. 4: 433 (1970). Also of interest with respect to the preparation of materials, such as porous or permeable materials for the manufacture of prosthetic devices and anatomical replacements, see U.S. Pat. Nos. 2,201,131, 2,490,193, 2,688,139, 2,860,175, 3,116,170, 3,201,282, 3,201,858, 3,215,563, 3,236,693, 3,242,011, 3,314,420, 3,400,719, 3,526,005, 3,526,906, 3,563,925 and 3,605,123. The disclosures of the above-identified patents and articles are herein incorporated and made part of this disclosure.

It is an object of this invention to provide useful three-dimensional porous, permeable structures.

It is another object of this invention to provide a method for the treatment of naturally occurring or synthetically prepared porous, permeable materials for the conversion of such materials into a structure providing a plurality of separate interpenetrating, three-dimensional channels or flowpaths, each of said channels or flowpaths being a closed system of connected porosity or permeability and interpenetrating said structure.

It is another object of this invention to provide apparatus and techniques for the utilization of the special structures prepared in accordance with this invention and described herein.

In at least one embodiment of this invention, at least one of the foregoing objects will be achieved.

Figure 7:
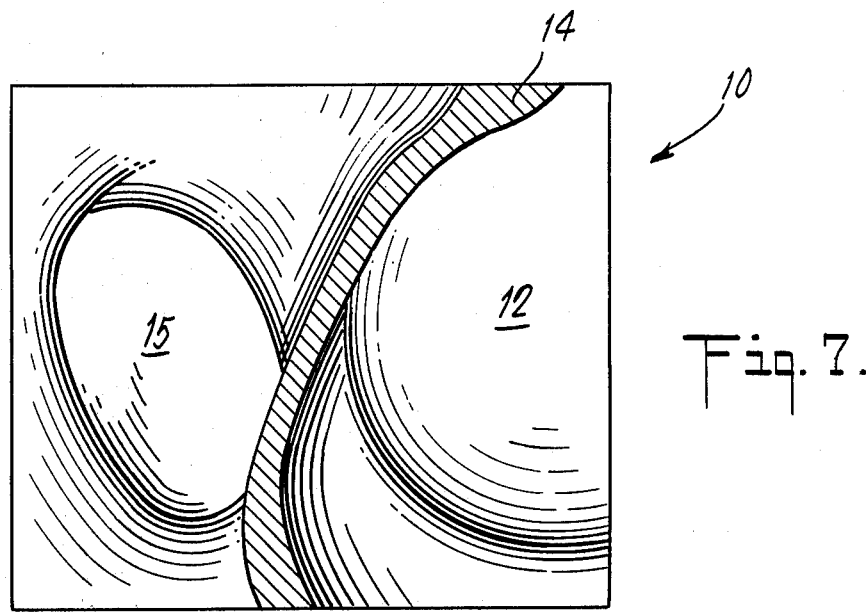
Figures 8, 9, 10:
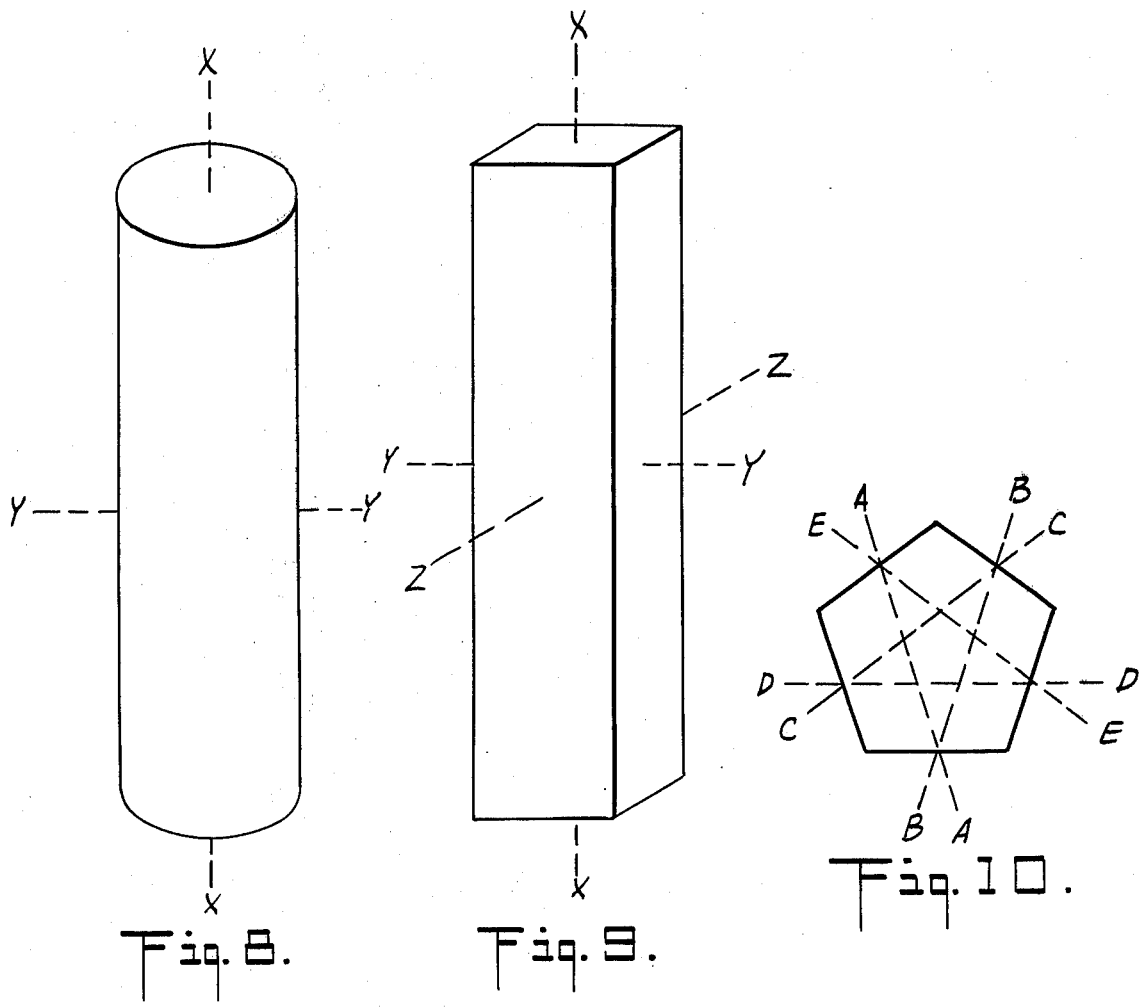

How these and other objects of this invention are achieved will become apparent from the resulting disclosure and drawings wherein:

FIGS. 1 – 6 schematically illustrate a technique in accordance with this invention for the production of a three-dimensional structure providing a plurality (2) of separate interpenetrating, three-dimensional channels or flowpaths, each channel or flowpath being a closed system of connected porosity or permeability and interpenetrating said structure;

FIG. 7 is a fragmentary cross-sectional drawing of a structure in accordance with this invention providing two separate flowpaths, the drawing of FIG. 7 being a magnified cross-sectional view;

FIG. 8 illustrates in perspective a cylindrical structure in accordance with this invention having two separate interpenetrating channels or flowpaths of connected porosity or permeability interpenetrating said structure and adapted such that one of said channels or flowpaths flows into and out of said structure only along the X-X axis or direction from one end to the other end of the cylindrical structure and the other or second channel or flowpath permits flow into and out of said structure only across said structure parallel to or along the Y-Y axis and transversely relative to the direction of flow in said one channel or flowpath.

FIG. 9 illustrates in perspective a quadrangular prism structure in accordance with this invention having three separate channels or flowpaths of connected porosity or permeability interpenetrating said structure and adapted such that the first of said flowpaths permits flow into and out of said structure only along the X—X axis or direction, the second channel or flowpath permits flow into and out of said structure only in the direction substantially transverse to said first channel or flowpath in the direction of the Y—Y axis and the third channel or flowpath permits flow into and out of said structure only in the direction substantially transverse to said first channel or flowpath and said second channel or flowpath and in the direction of the Z—Z axis.

Figure 11:
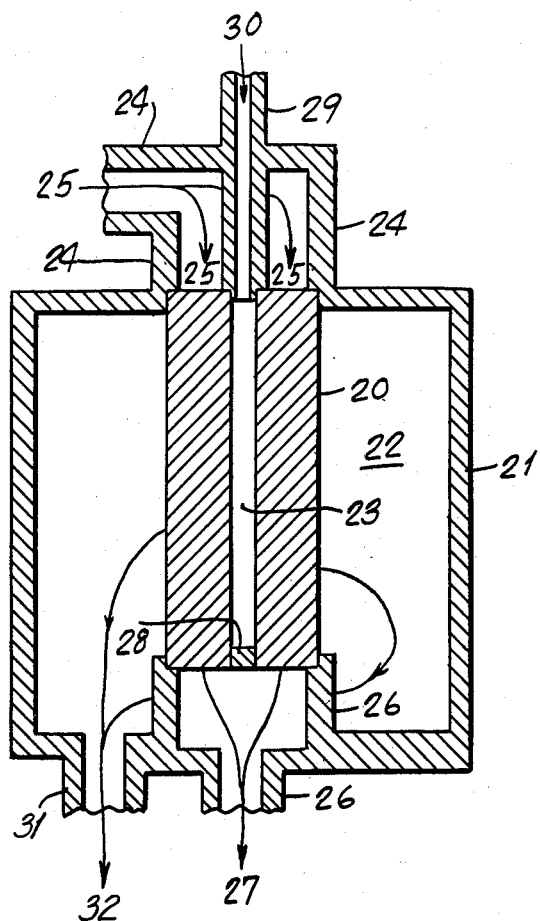

FIG. 10 illustrates in cross-section a pentangular prism structure in accordance with this invention provided with five separate channels or flowpaths each of connected porosity or permeability and interpenetrating said structure, the structure being adapted such that the first of said channels or flowpaths permits flow only in the direction A—A axis, the second permits flow only in the direction B—B axis, the third only in the direction C—C axis, the fourth only in the direction D—D axis and the fifth only in the direction E—E axis, each channel or flowpath providing a flowpath direction substantially transverse to every other channel or flowpath; and FIG. 11 illustrates an apparatus including a tubular or hollow cylindrical structure in accordance with this invention for the treatment or handling of a fluid (gas and/or liquid), such as a body fluid.

Three dimensional materials or structures providing a plurality of separate interpenetrating, three-dimensional domains or channels or flowpaths, each of said domains or channels or flowpaths being a closed system of connected porosity or permeability and interpenetrating said structure, have been prepared. The aforesaid structures may possess or be characterized as having two or more separate interpenetrating channels or flowpaths, such as 2, 3, 5 or more, as may be desired in the manufacture or preparation of such structures in accordance with this invention and/or as may be required for the purpose or use to which the structures are to be put or applied.

The special materials or structures of this invention may possess substantially any desired configuration or shape. The materials or structures of this invention may be cylindrical in shape, solid or hollow or tubular, may be in the shape of a prism, such as a triangular prism, a quadrangular prism, a pentagonal prism and the like or prismoid or sperical or ellipsoid in shape and, indeed, may possess substantially any desired height, width, depth or thickness or external configuration.

Naturally occurring and synthetically prepared or manufactured three-dimensional materials or structures which provide a single domain or channel or flowpath which is a closed system of connected porosity or permeability interpenetrating said material or structure are known, see U.S. Pat. Nos. 3,890,197 and 3,929,971. Such materials are also found in nature, particularly in the calcium carbonate porous skeletal material of marine life, such as the reef building colonial coral Porites as well as the echinoderm skeletal material. Such skeletal materials, see *Science*, Vol. 166: 1147 (1969), possess a microstructure characterized by a pronounced three-dimensional fenestrate structure providing a periodic minimal surface. Such a surface divides the structure into two interpenetrating regions, one a solid, each of which is a single multiple-connected domain. Such materials are not unique with respect to overall porosity and permeability since other materials also are available which possess a single three-dimensional channel or flowpath of connected porosity or permeability interpenetrating the structure or material. For example, a material having a single channel or flowpath of the type disclosed herein of connected porosity and interpenetrating the material or structure may be prepared by bringing together and fusing at points particles of material such that the resulting formed material is permeable and there is provided therein a single channel or flowpath with multiple interconnections extending throughout the material or structure and possessing a connected porosity or permeability. What is unique, however, about the echinoderm skeletal material, as with the coral Porites skeletal material, is the uniformity of pore size and their microstructures.

In connection with the manufacture of porous permeable material for implants or prosthetic materials, it is desirable to have pore connections of micron size, such as in the range 100–200 $\mu m$ (micron). The optimum pore size for the ingrowth of osteoid cells and fibrous tissue is in the range 100–500 $\mu m$ and 5–75 $\mu m$, respectively. These pore sizes and resulting permeabilities are difficult to obtain from synthetically prepared or manufactured materials but are provided in the porous permeable skeletal material of marine life, such as in the microstructures of echinoid spine calcite material, coral Porites skeletal aragonite material and the like. Such materials provide a microstructure having a single channel or flowpath therein of connected porosity or permeability interpenetrating the material or structure with pore connections or pore openings in the range about 5–500 microns with sections or portions of substantially uniform porosity and uniform pore volume, such as in the range 10 to about 90%. The solid material making up such structures and defining the single flowpath of connected porosity or permeability and like the flowpath is connected, continuous and interpenetrating throughout the structure such that, also like the flowpath defined by the material making up the structure, there are substantially no discontinuities in the solid material making up such materials.

These skeletal materials are preferred as precursor materials in the practices of this invention because of their highly unusual microstructure which provides a pore size over a substantial range, 5–500 microns, with portions of such materials having substantially uniform porosity and/or pore volume, e.g. in the range 10–90%. Synthetically prepared materials having such a range of pore size and corresponding permeability and range of pore volume, either uniform or varying, are difficult to prepare. Moreover, since such natural skeletal materials are usually comprised of calcium carbonate, these materials are easily handled and shaped and can be readily treated by chemical dissolution or etching in accordance with the practices of this invention to clean and/or remove the calcium carbonate when desired.

The practices of this invention in one of its embodiments for the manufacture of a material or structure having a plurality, in this instance two, of separate interpenetrating, three-dimensional channels or flowpaths, each of said channels or flowpaths being a closed system of connected porosity or permeability interpenetrating the structure, are schematically illustrated in FIGS. 1 – 6 of the drawings.

Referring now to FIGS. 1 – 6 of the drawings, there is illustrated therein a technique in accordance with one embodiment of the practice of this invention for the manufacture of the special materials described herein. FIG. 1 shows schematically in cross-section a structure generally indicated by reference numeral 10, such as may be obtained from the porous carbonate skeletal material of marine life, e.g. echinoid spine calcite or coral skeletal aragonite, in one stage of treatment in accordance with this invention. Solid material 11, such as calcium carbonate, makes up structure 10 and defines connected pores 12 which are shown filled with a curable or settable fluid or liquid 14 as indicated by cross-hatching. The settable or curable liquid is also shown coating the outside of structure 10. Structure 10 schematically illustrated in FIG. 1 can readily be obtained from coral Porites skeletal material by cutting and shaping it to a desired shape and then thoroughly cleaning the resulting shaped skeletal material for the removal of any organic material which might be occupying a portion of the pores thereof by immersing the piece in a 10% aqueous sodium hypochlorite, followed by rinsing and drying.

Figure 2:
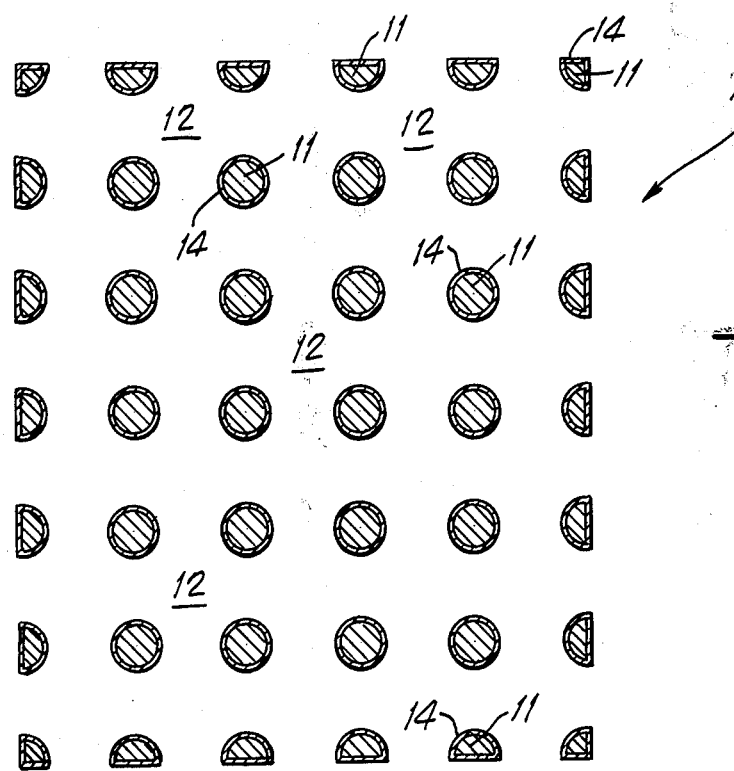

When structure 10, as illustrated in FIG. 1, has been treated so as to be substantially completely impregnated with curable or settable liquid 14, the structure is then spun or centrifuged so as to remove therefrom curable or settable liquid 14 occupying pores 12 thereof. Pores 12 would then be emptied, leaving a residual coating 14 of the curable or settable liquid on solid material 11 defining structure 10 and connected pores 12 thereof, as illustrated in FIG. 2. The residual coating or settable liquid would then be cured or set, thereby providing a continuous solid coating 14 on material 11 defining connected pores 12.

Figure 3:
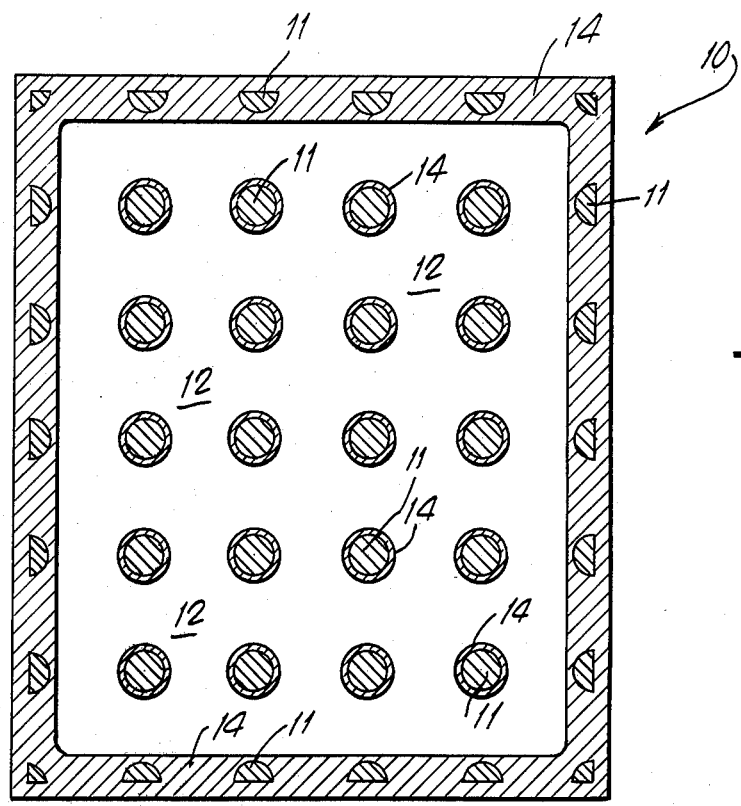
Figure 4:
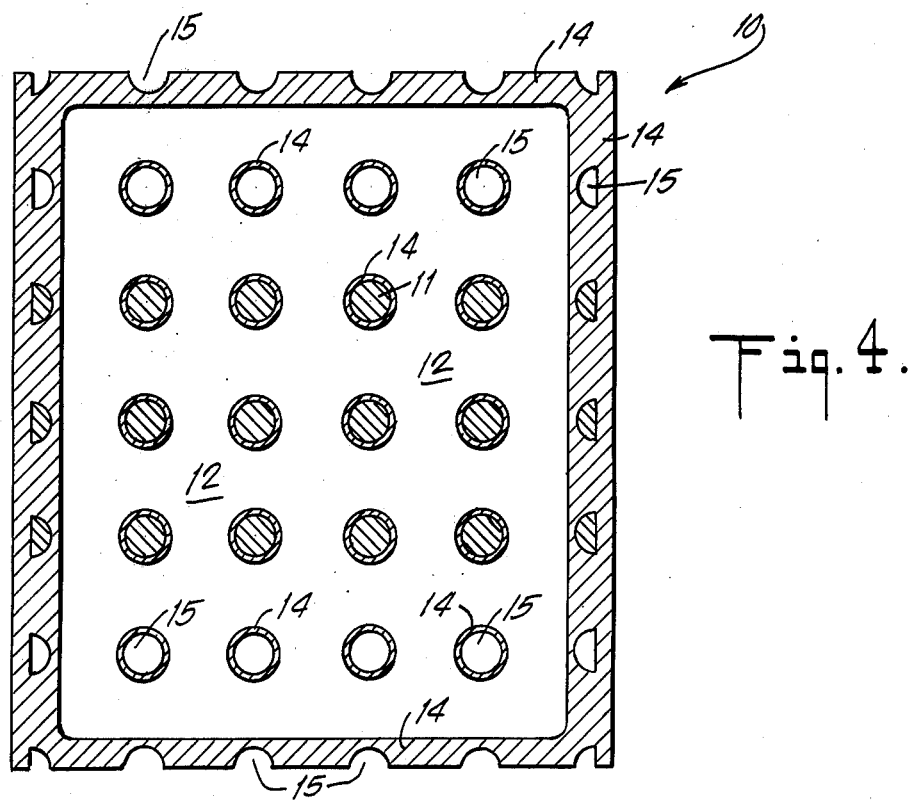

Referring now to FIG. 3, after structure or piece 10 has been emptied of the curable or settable liquid and the resulting coating of curable or settable liquid on the structural solid material 11 has been cured and set thereon, as illustrated in FIG. 2, treated structure 10 is skin coated or skin filled with additional curable or settable liquid, as illustrated in FIG. 3. As illustrated in FIG. 3, structure 10 is now substantially encapsulated within a skin filling of curable or settable liquid 14 which is then cured or set, the peripheral or outside pore connections and the peripheral outside solid material 11 being occupied and coated by the cured or set curable or settable liquid 14, as illustrated. The cured or set liquid, now solidified, encapsulates resulting treated structure or piece 10. Structure 10 illustrated in FIG. 3 is then treated, as illustrated in FIG. 4, by removing from the top and bottom thereof a portion of the encapsulating coating 14 to expose material 11, e.g. calcium carbonate, which is then skin acid etched or dissolved, such as by contact with a dilute solution of hydrochloric acid, with the result that the outside peripheral portion of material 11 at the top and bottom of structure 10 is removed, including an adjacent portion thereof, as illustrated, thereby opening channel 15 from the outside of structure 10 to the inside thereof for a short distance. Channel 15 is defined by the cured or set solid material 14, as indicated by reference number 14. As illustrated in FIG. 4, both the top and bottom or opposite sides of structure 10 are similarly treated.

Figure 5:
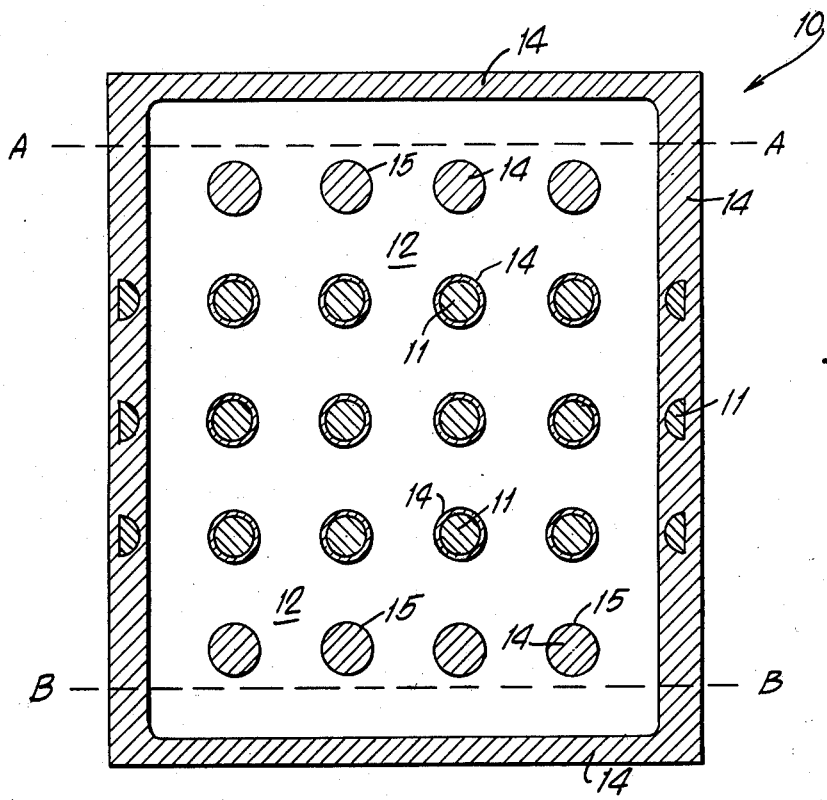

The resulting treated structure 10 illustrated in FIG. 4 is then skin filled or impregnated at the top and bottom or opposite ends thereof with additional curable or settable liquid 14 and the curable or settable liquid again cured or set to produce the encapsulated structure or piece illustrated in FIG. 5, with the cured or set liquid (solidified) occupying just opened or created channel 15. Thereupon, a portion of the top and bottom ends thereof is cut away along dashed lines A—A and B—B, as illustrated in FIG. 5.

Figure 6:
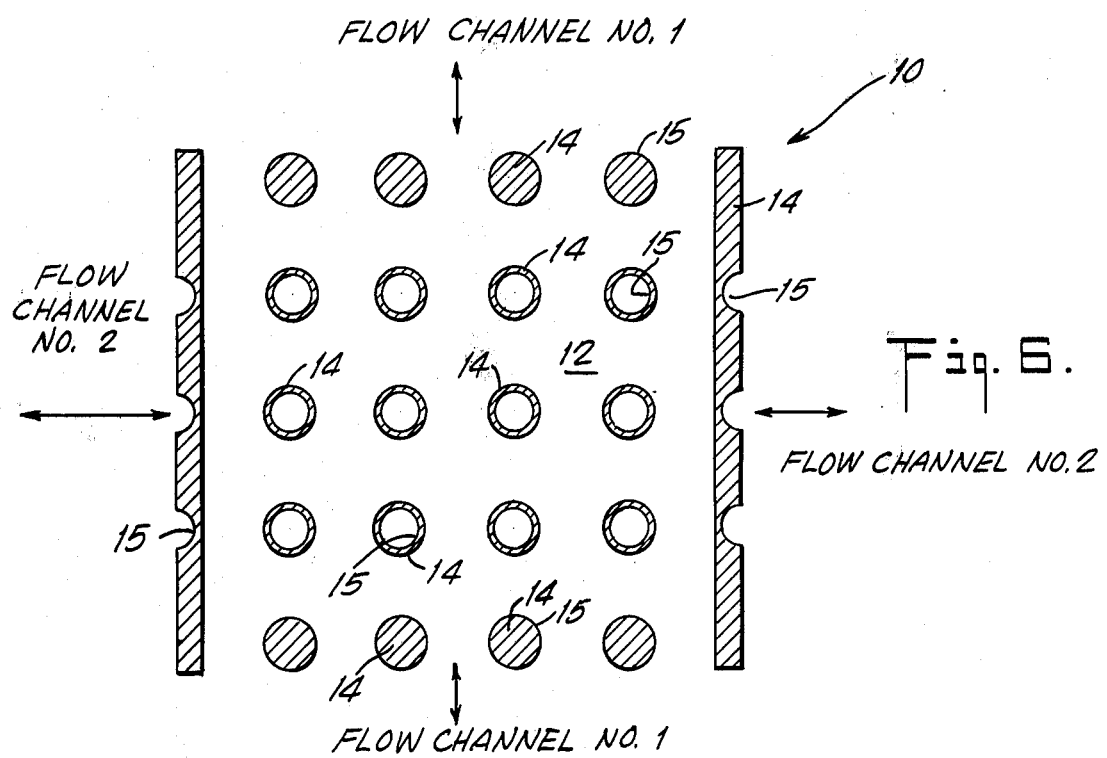

Structure 10, illustrated in FIG. 5, after cutting along lines A—A and B—B, exposes a first separate interconnected continuous flow channel made up of connected pores 12. Thereupon, as illustrated in FIG. 6, the cured or set solid material 14 encapsulating the sides of structure 10 would be trimmed or cut away to expose material 11 which would then be chemically etched or dissolved away to open up a second channel of connected porosity or permeability, which second channel had been previously occupied in structure 10 by the three-dimensional interconnected and interpenetrating continuous network of solid material 11, see FIG. 1, originally making up structure 10. Since, however, solid material 11 had been coated with cured or set solid material, substantially impervious and inert to the solvent or etching liquid employed to remove the original solid material 11, the second channel opened up would be defined by coating 14 as illustrated. Accordingly, the substantially finished piece or structure 10 illustrated in FIG. 6 provides two separate interconnected three-dimensional flowpaths or channels of connected porosity or permeability interpenetrating piece or structure 10, one flowpath, flow channel No. 1, permitting flow in the direction lengthwise of structure 10 from one end to the other end via the original, now exposed, connected pores 12. The other flowpath, flow channel No. 2, permits flow crosswise of finished structure 10, i.e. substantially transversely of flow channel No. 1, within the space previously defined by material 11, the calcium carbonate originally making up the solid phase of structure 10 but which after having been coated with solid 14 has been removed by chemical etching or dissolution. Since the outside or peripheral portions of flow channel No. 2 at the top and bottom ends of finished structure 10 are blocked by cured solid material 14, as illustrated in FIG. 6, there would be no way for escape of fluid flowing through flow channel No. 2 into the fluid flowing through flow channel No. 1. In effect, finished structure 10 is now constituted or comprised of cured solid material 14 which defines both flowpaths, flow channel No. 1 and flow channel No. 2. Within structure 10, flow channel No. 1 is defined by the outside surface of solid material 14 and flow channel No. 2 is defined by the inside surface of hollow solid 14. Both flow channels are separate and possess continuous connected porosity and permeability and interpenetrate finished structure 10, as illustrated.

FIG. 7 illustrates by way of a drawing a cross-sectional view of the internal structure of a fragment of the finished structure 10 of FIG. 6 illustrating solid material 14 defining flow channel No. 2 identified by reference numeral 15 defined by solid material 14 which coated the original material 11, e.g. calcium carbonate of original structure 10, see FIG. 1. The other flowpath, such as flow channel No. 1, also defined by solid material 14, is identified by reference numeral 12. Flow channel No. 1 is essentially the original connected pore volume 12 of original structure 10, see FIG. 2.

FIG. 8 shows one embodiment of a structure in accordance with this invention having two separate channels or flowpaths of the type described herein. As illustrated in FIG. 8, the structure is a right angle cylinder and may be adapted in accordance with the practices of this invention described in connection with FIGS. 1 - 6 to provide a flowpath only along the central or longitudinal axis X—X and a separate flowpath substantially transversely thereof only along the Y—Y axis. If desired, the solid right angle cylinder of FIG. 8 could be hollow or tubular in shape. The structure illustrated in FIG. 8 is readily prepared, as indicated, by following the operations or techniques illustrated in FIGS. 1 - 6 of the drawings and described herein.

A structure having three separate channels or flowpaths of the type described herein is illustrated in FIG. 9 and can be prepared or adapted in accordance with the practices of this invention to provide a three channel structure, as illustrated in FIG. 9, which permits flow via a first channel only along the longitudinal or central axis X—X and flow via a second channel only along the Y—Y axis substantially transverse or perpendicular to the X—X axis and flow via a third channel only along the Z—Z axis substantially transverse with respect to the flow via the first and second channels.

A structure such as is illustrated in FIG. 9 is prepared in accordance with the practices of this invention by further modifying a finished structure of the type illustrated in FIG. 6, the structure having been modified by cutting away the top and bottom portions closing off flow channel No. 1. As described hereinabove in connection with FIGS. 1 - 6, the modified structure is then impregnated to coat both flowpaths, flow channel No. 1 and flow channel No. 2 of the modified structure, with a second or different settable or curable liquid which would then be set or cured to a solid coating. The solid material originally making up the modified structure would be removed by suitable means, e.g. chemical etching or dissolution. When this is done, there would be produced a structure having three separate flowpaths or channels which could then be further treated in accordance with the practices of this invention to produce a structure as illustrated in FIG. 9 which yields a three separate flow channel structure permitting separate overall flow only in the directions of the X—X, Y—Y and Z—Z axes.

The above procedure described in connection with FIG. 9 could again be repeated, i.e. employing yet another settable or curable liquid which would be employed to coat the surfaces making up the special three channel structure of FIG. 9, which is illustrated in perspective as a quadrangular prism structure. By employing yet another different curable or settable liquid and solidifying the same after the surfaces of the three channel structure have been coated and removal of the pre-existing solid material, there is produced a structure having five separate channels or flowpaths of connected porosity or permeability interpenetrating the structure. Such a structure adapted for five separate directed flowpaths is illustrated in cross-section in FIG. 10, the cross-section of the pentagonal prism with the five separate flowpaths therein being along the A—A direction or axis, the B—B direction or axis, the C—C direction or axis, the D—D direction or axis and the E—E direction or axis. If desired, structures providing a still larger number of separate flow channels can be prepared in accordance with the practices of this invention.

In the practices of this invention for the preparation of a structure having a plurality, two or more, of separate interpenetrating, three-dimensional channels or flowpaths, each channel or flowpath being a closed system of connected porosity or permeability, see FIG. 1 – 6, and the foregoing portion describing the technique illustrated in FIGS. 1 – 6 for the manufacture of a structure having two separate interpenetrating channels or flowpaths with the structure being further adapted or modified such that fluids entering and leaving said structure enter and leave separate portions thereof, it is disclosed that in the manufacture of such a structure a curable or settable liquid is employed to coat the precursor material which is provided with only one channel or flowpath of the type described herein. Various useful and suitable curable or settable liquids which are curable or settable to a cured or solid material are useful. Suitable such curable or settable liquids include a liquid silicon rubber which is curable to a solid silicon rubber. Also useful are fluid urethane or polyurethane materials or fluids which are curable to solid polyurethane materials. Many other curable or settable liquids which are cured or set to a solid material for forming a continuous coating on solid surfaces to which such curable or settable liquids are applied are useful in the practices of this invention.

In addition to curable or settable liquids, other techniques and materials may be employed to coat the precursor material in accordance with the practices of this invention for the conversion of, for example, a single channel or flowpath precursor material, e.g. coral Porites carbonate skeletal material, to a material having two separate channels or flowpaths. Such suitable techniques would include vapor phase deposition of a metal or other vaporizable solid material onto the surfaces making up the precursor material. The vapor phase deposited material need not be a metal as indicated but could indeed be any material which, when applied in vapor form, condenses into the surfaces in contact therewith to build up thereon a continuous solid coating. Another technique useful in the treatment of precursor material for the manufacture of the special materials and structures of this invention includes deposition or precipitation of solid materials from a carrier liquid introduced into contact with the precursor material. A suitable technique along this line would be autocatalytic deposition of a metal from solution or the electrodeposition of a material or metal from solution.

It is pointed out that multiple coatings, the same or different materials, can be deposited upon the precursor materials thereof for control of pore size. This technique would be particularly applicable wherein one or more applications of a curable or settable liquid is employed to coat the surfaces of the precursor material.

The following is an example of the technique illustrated in FIGS. 1 – 6 of the drawings and described hereinabove for the manufacture of a two flowpath structure in accordance with this invention having controlled access and egress for two separate fluid streams.

A clean cylinder, such as is provided by coral Porites skeletal aragonite (calcium carbonate) material, is prepared. The cylinder is then impregnated or injected with a silicon rubber polymer, e.g. Dow Corning MDX-4-4210 silicon rubber, and then centrifuged at about 2000 rpm at a 25 cm radius for one hour leaving a coating on the internal surfaces of the cylinder of the liquid rubber of about 1 $\mu$m thick, which coating is then cured and set to a solid. The original void space or surface pores on all surfaces would then be skin filled and closed by immersing the cylinder in the liquid rubber polymer (Dow Corning MDX-4-4210 silicon rubber) at a low pressure, about 470 mm Hg. and then bringing the pressure up to atmospheric, about 760 mm Hg. over a period of one-half hour so as to completely occupy the surface pores and to coat the cylinder for a depth of about 1 mm. The cylinder is then treated to close off or fill the original carbonate solid material at the ends and to reopen the pore spaces, including acid etching the carbonate phase at the ends of the cylinder to a depth beyond the original pores filled with rubber employing 2% hydrochloric acid for 2 hours with the resulting removal of the carbonate phase to a depth of about 4 mm. The treated cylinder would then be immersed in the liquid silicon rubber polymer at a reduced pressure, about 380 mm Hg. and the pressure gradually increased to atmospheric, about 760 mm Hg. over a half-hour period, thereby filling the etched carbonate phase to about 2 mm. Thereupon, about 1.5 mm portions of the ends would be cut off, such as by a microtome, exposing the original pore space but not the solid phase. Subsequently, the solid carbonate phase would be removed by an acid etch with the result that there would be produced a structure having two separate flowpaths in accordance with this invention, one flowpath having ingress and egress from the ends and the other flowpath having ingress and egress from the sides of the cylinder.

Structures having a plurality of separate flowpaths or channels in accordance with this invention can be prepared in various sizes from a diameter or length as small as about 15 $\mu$m including thinned wall structures, such as tubular structures having a wall thickness as low as about 0.5 $\mu$m useful in biomedical applications to relatively large structures measuring a foot or more in width or diameter and/or many feet in length and useful in industry as mixers, heat exchangers, etc. Such structures permit or provide a high internal surface area per unit in volume with interconnections as little as 15 $\mu$m apart. The structures in accordance with this invention, as indicated hereinabove, can be manifolded or adapted such that the flowpaths or channels therein maintain the fluids flowing therethrough separate and without crossover or mixing unless desired or in the instance where a channel is defined or made up of a material which is selectively permeable to one or more of the components of a fluid flowing through the channel so defined or an adjacent channel. For example, the structures prepared in accordance with this invention can employ an exchange membrane in its make-up through which ions or atoms or molecules in one of the fluid (liquid) phases flowing therethrough can diffuse through the membrane defining the structure to an adjacent flowpath or channel. Such structures can be prepared in accordance with this invention to provide a very high surface area for exchange in a small volume.

The three-dimensional character of the structure effectively struts or maintains the membrane and structure making it feasible to utilize a much thinner membrane than would heretofore appear to be possible without tearing or collapsing. Accordingly, because small structures in accordance with this invention can be prepared, such structures can be usefully employed in vivo, i.e. implanted in a host, such as in a human body, with suitable connections, internally or externally, thereof for the supply of fluids, such as a body fluid, e.g. blood, to one of the separate channels or flowpaths and for the supply of another fluid, such as another body fluid stream or fluid supplied from a reservoir, either internally or externally, for the treatment of, for example, the body fluid flowing through the implanted structure. If desired, the structure need not be implanted but could be extra-corporeal with suitable connections to and from the body for the supply of body fluids thereto and/or other fluids.

Reference is now made to FIG. 11 of the drawings which shows one embodiment of the practices of this invention, employing a special structure prepared in accordance with this invention, see FIGS. 1 - 6.

As illustrated in FIG. 11, tubular structure 20 is fluid-tightly fitted at its ends within closed chamber 21 to provide an annular space 22 between the inside of the surface of chamber 21 and the outside surface of tubular structure 20. Tubular structure 20 provides two separate channels or flowpaths and is adapted in accordance with this invention such that one flowpath extends longitudinally thereof from one end to the other end and the other flowpath extends radially or transversely thereof with respect to the first-mentioned flowpath such that fluid introduced into tubular structure 20 at one end thereof travels therethrough and emerges only at the other end thereof and fluid, such as another fluid, introduced from the inside of structure 20 emerges transversely thereof on the outside thereof.

More particularly, as illustrated in FIG. 11, annular flow inlet means 24 is provided on the top of chamber 21 for the introduction of a first fluid stream via flowpath 25 as indicated for introduction into the top end of tubular structure 20. The fluid thus introduced emerges from tubular structure 20 only at the bottom end thereof from outlet 26 via flowpath 27. As illustrated, a fluid-tight seal is provided between the bottom end of tubular structure 20 and outlet 26 including sealing means or plug 28 fluid-tightly fixed at the bottom of the space 23 provided within the interior of tubular structure 20. Fluid is supplied to interior space 23 of tubular structure 20 via separate central inlet conduit 29 provided within inlet 24 such that fluid supplied via inlet conduit 29 enters into the space 23 within tubular structure 20 via flowpath 30 and flows outwardly of structure 20 into annular space 22 and is removed through outlet 31 provided in the bottom of chamber 21 via flowpath 32. The two separate flowpaths for ingress and egress of the separate fluid streams are schematically illustrated in the the drawing, see the flow lines indicated by the arrows.

The apparatus illustrated in FIG. 11 and embodying special structure 20, a structure prepared in accordance with one embodiment of this invention possessing two separate flowpaths as described hereinabove, has many uses. For example, the apparatus of FIG. 11 could be used as a heat exchanger by introducing a fluid, such as a cold liquid, through inlet 29 via flowpath 30 and by introducing relatively hot liquid through inlet 24 via flowpath 25 and separately recovering these two liquids, the liquid introduced via inlet 29 now having an increased temperature upon recovery from outlet 31 via flowpath 32 and the fluid introduced via inlet 24 now having a reduced temperature upon recovery from outlet 26 via flowpath 27.

The apparatus illustrated in FIG. 11 could be employed for the separate mixing of separate multi-component streams while at the same time maintaining each multi-component stream separate, the mixing of each multi-component stream being effected upon separate passage through tubular structure 20 as illustrated.

The apparatus of FIG. 11 could also be employed for carrying out chemical reactions under controlled temperature conditions wherein one chemical reaction is carried out in one of the separate flowpaths and the temperature of this chemical reaction being controlled by heat exchange with a fluid or liquid stream flowing through the other adjacent flowpath.

As indicated herein, the apparatus of FIG. 11 may be relatively large in size with chamber 21 being a few inches in diameter, about 3 inches, to about a few feet, 3 feet in diameter, and a length from about 6 inches to about 6 feet, respectively. The size of the apparatus illustrated in FIG. 11 may also be quite small, such as a size suitable for implantation in a host, such as the human body, such as dimensions in the range from about ⅜ of an inch in diameter to 1-2 inches long, or smaller or larger as may be desired or required.

The apparatus of FIG. 11 could be employed in biomedical applications, such as for oxygenation of human blood, dialysis of human body fluids, hyperalimentation for therapeutic purposes and the like. For example, flowpath 25 via inlet 24 could serve for the introduction of a gas, such as oxygen, dialysis preparations or solutions, hyperalimination solutions, special drugs or antibody preparations and flowpath 30 via inlet 29 could serve for the introduction of a body fluid, such as human blood, arterial or venous, for recovery via outlet 31 and flowpath 32. An apparatus for such uses could be maintained and/or operated outside of the body or implanted in the body with suitable fluid connections to and from the apparatus. The apparatus of FIG. 11, for example, could easily be adapted to current arteriovenous fistula technology and could be adapted for quick exchange or replacement when necessary including quick exchange or replacement of the special flow structure or membrane structure 20. By providing structure 20 possessing two separate flowpaths with a special membrane, such as silicon rubber defining these flowpaths, the membranes being selected to permit passage of a desired substance, e.g. ions, molecules of selected molecular weight, amino acids or a gas, such as oxygen, or a drug would permit the following biomedical applications.

For example, the apparatus of FIG. 11 could be adapted as a lung bypass. Membranes are known which are selectively permeable to oxygen and which can function as a total lung bypass for extended periods to aid in the resolution of serious or heretofore terminal lung diseases, e.g. severe viral pneumonia, or to provide continuous support in chronic lung diseases, such as chronic obstructive pulmonary diseases. The high surface area structural materials making up structure 20 of FIG. 11 permits miniaturization of the apparatus and structure 20 would permit a total implantable pulmonary bypass. Also, as indicated hereinabove, miniaturization of the apparatus of FIG. 11 and components thereof or associated therewith would permit the use of the apparatus as an implantable dialysis membrane. Additionally, in those diseases, such as diabetes and hypothyroidism which are treatable by replacement of specific hormones, insulin or thyroid, sensing devices associated with the device of FIG. 11 designed to determine and respond to the body fluid or blood level compositions would permit implantable drug dispensing or release systems, which apparatus could then function as an artificial pancreas or thyroid.

The apparatus of FIG. 11 could also be used for total parenteral feeding as a means of providing nutrition in chronic debilitating diseases, such as the treatment of short bowel syndromes. A problem heretofore experienced in hyperalimentation treatments and apparatus has been sepsis due to bacterial contamination of the hyperalimentation sites. Implantable structures, such as structure 20 and the apparatus of FIG. 11, would serve to lock out or prevent bacterial transport or access but allow passage of the vital nutrients, e.g. amino acids, etc., employed in the hyperalimentation program.

The special structures of this invention, such as structure 20, could also be employed in cell culture and antibody transfusion systems wherein specific cell lines, e.g. normal lymphocytes of patients with leukemia would be grown in the patients' own nutrient bath or body fluid and then transfused to the body fluids while malignant lines are eliminated, such as by radiation or chemotherapy or immunotherapy. A very specialized adaptation of the structures, such as structure 20 and the apparatus of FIG. 11 of this invention, would be to use structure 20 to continuously transfuse via the membrane defining the separate flowpaths therein, anti-tumor antibodies in cancer patients or specific blocking factors to antibodies produced in organ transplant patients to alleviate substantially all phases of organ rejection phenomena. Other uses of the highly specialized structures of this invention and apparatus embodying the same are possible, beyond industrial uses, such as for the manufacture of specialty chemicals or for carrying out or controlling special or sensitive chemical reactions and for other biomedical purposes.

As will be apparent to those skilled in the art in the light of the foregoing disclosure, many modifications, alterations and substitutions are possible in the practice of this invention without departing from the spirit or scope thereof.

We claim:

1. An integral three-dimensional structure providing a plurality of separate interpenetrating, three-dimensional domains or channels, each of said domains or channels being a closed system of connected porosity or permeability with multiple interconnections only with respect to its respective domain or channel, each of said domains or channels being interpenetrating within said structure.

2. A structure in accordance with claim 1 wherein said integral structure is made of the same material.

3. A structure in accordance with claim 1 wherein each of said domains or channels is provided with outlets on the surface of said structure.

4. A structure in accordance with claim 1 wherein at least one of said domains or channels or flowpaths is provided with outlets on the surface of said structure.

5. A structure in accordance with claim 1 wherein said structure is made of different materials.

6. A structure in accordance with claim 1 wherein the walls of at least one of the separate interpenetrating, three-dimensional domains or channels or wherein at least one of said domains or channels is defined or made up of material which is selectively permeable.

7. A structure in accordance with claim 1 wherein there are provided two separate interpenetrating, three-dimensional domains or channels.

8. A structure in accordance with claim 1 wherein there are provided three separate interpenetrating, three-dimensional domains or channels.

9. A structure in accordance with claim 1 wherein fluid supply means are provided on a portion of the outside surface of said structure for the supply of fluid to only one of said domains or channels.

10. A structure in accordance with claim 1 wherein separate fluid supply means are provided on a portion of the outside surface of said structure for the supply of fluid to each of said domains or channels.

11. A structure in accordance with claim 1 wherein said structure is substantially tubular in shape.

12. A structure in accordance with claim 1 wherein said structure is substantially cylindrical in shape.

13. A structure in accordance with claim 1 wherein said structure is a prism.

14. A structure in accordance with claim 13 wherein said prism is a quadrangular prism.

15. A structure in accordance with claim 13 wherein said prism is a pentagonal prism.

16. A structure in accordance with claim 1 wherein the walls defining at least one of the separate interpenetrating, three-dimensional domains or channels or wherein at least one of said domains or channels is defined or made up of a material which comprises dispersed or admixed therein a reagent capable of slow release from said walls of said material.

17. A structure in accordance with claim 1 wherein at least one of said domains or channels is provided with separate fluid supply and exit means on the surfaces of said structure such that fluid supplied via said separate fluid supply means exits from said structure only via said fluid exit means.

18. A structure in accordance with claim 7 wherein each of said two separate interpenetrating, three-dimensional domains or channels is provided with separate fluid supply and exit means such that fluid supplied to each of said fluid supply means exits from said structure only from its corresponding fluid exit means.

19. A structure in accordance with claim 8 wherein each of said three separate interpenetrating, three-dimensional domains or channels is provided with separate fluid supply and exit means such that fluid supplied to each of said supply means exits from said structure only from its corresponding fluid exit means.

20. A structure in accordance with claim 1 wherein each of the domains or channels making up said plurality of separate interpenetrating, three-dimensional channels or flowpaths of said structure is provided with separate fluid supply and corresponding separate exit means such that fluid supplied to each of said supply means exits from said structure only from its corresponding fluid exit means.

21. A method of transferring or transporting a component of one flowing fluid stream to another flowing fluid stream without physically intermingling or mixing said streams which comprises flowing said one fluid stream containing said component through a first separate interpenetrating, three-dimensional channel or flowpath provided within a structure having an inlet and outlet only for said one fluid stream, flowing said other fluid stream through a second separate interpenetrating, three-dimensional channel or flowpath also provided within said structure and having an inlet and outlet only for said other fluid stream, the walls of said first channel or flowpath being defined by or made up of a material which is selectively permeable for said component such that as the first stream containing said component flows through said first channel or flowpath said component permeates or moves through said selectively permeable material making up or defining the walls of said first channel or flowpath into said other fluid flowing through said other channel or flowpath.

22. A method in accordance with claim 21 wherein said one fluid stream is a human body fluid.

23. A method in accordance with claim 22 wherein said human body fluid is arterial blood or venous blood.

24. A method in accordance with claim 21 wherein said other fluid stream is a human body fluid.

25. A method is accordance with claim 24 wherein said human body fluid is arterial blood or venous blood.

26. A method in accordance with claim 21 wherein said first fluid stream is an oxygen-containing stream, said oxygen being present therein as dissolved oxygen or gaseous oxygen, and wherein said other fluid stream is a human blood stream, said selectively permeable material making up the walls of said first channel or flowpath being permeable to oxygen.

27. A method in accordance with claim 21 wherein said component in said first fluid stream is a bio-affecting component and wherein the other fluid stream is a human blood stream.

28. A method in accordance with claim 27 wherein said bio-affecting component comprises one or more amino acids suitable for hyperalimentation.

29. A method in accordance with claim 27 wherein said bio-affecting component is a human hormone.

30. A method in accordance with claim 27 wherein said bio-affecting component is an antibiotic or antibacterial or antiviral material.

* * * * *

UNITED STATES PATENT AND TRADEMARK OFFICE
CERTIFICATE OF CORRECTION

PATENT NO. : 4,075,092
DATED : February 21, 1978
INVENTOR(S) : Eugene W. White et al It is certified that error appears in the above-identified patent and that said Letters Patent are hereby corrected as shown below:

Col. 2, line 53, "sperical" should read -- spherical --

Col. 4, line 24, after "hypochlorite" the word -- solution -- should be inserted Col. 11, line 50 (Claim 4), after "channels" the words "or flowpaths" should be deleted Signed and Sealed this Twenty-first Day of November 1978

[SEAL]

Attest:

RUTH C. MASON
Attesting Officer

DONALD W. BANNER
Commissioner of Patents and Trademarks